US005589457A

United States Patent [19]
Wiltbank et al.

[11] Patent Number: 5,589,457
[45] Date of Patent: Dec. 31, 1996

[54] PROCESS FOR THE SYNCHRONIZATION OF OVULATION

[75] Inventors: Milo Wiltbank, Madison; James R. Pursley, Sun Prairie, both of Wis.

[73] Assignee: Ausa International, Inc., Tyler, Tex.

[21] Appl. No.: 498,691

[22] Filed: Jul. 3, 1995

[51] Int. Cl.$^6$ .................... A61K 38/24; A61K 31/19
[52] U.S. Cl. ................. 514/12; 514/15; 514/573
[58] Field of Search ................ 514/12, 573, 15

[56] References Cited

U.S. PATENT DOCUMENTS

| | | | |
|---|---|---|---|
| 4,780,451 | 10/1988 | Donaldson | 514/12 |
| 4,845,077 | 7/1989 | Hodgen | 514/2 |
| 5,180,711 | 1/1993 | Hodgen | 514/15 |
| 5,288,705 | 2/1994 | Zohar | 514/15 |
| 5,378,688 | 1/1995 | Nett | 514/15 |

OTHER PUBLICATIONS

Pursley et al., J. Anim. Sci. (72) Suppl. 1/J. Dairy Sci. (77) Suppl. 1/1994, 69.

*Primary Examiner*—Phyllis G. Spivack
*Attorney, Agent, or Firm*—William D. Jackson; Harris, Tucker & Hardin, P.C.

[57] ABSTRACT

A method for synchronizing ovulation in cattle by sequential injection of hormones is disclosed. A hormone selected from the group consisting of gonadotropin releasing hormone (GnRH), luteinizing hormone (LH), or human chorionic gonadotropin (hCG) is administered to an open cow during an estrous cycle in order to stimulate follicle development. Prostaglandin $F_{2\alpha}$ ($PGF_{2\alpha}$) is then administered to initiate corpus luteum regression about five to eight days after administration of the GnRH, LH or hCG. A second dose of GnRH, LH or hCG is then administered concomitantly with the $PGF_{2\alpha}$ injection or up to about three days after the $PGF_{2\alpha}$ injection. This second dose of hormone functions to stimulate the ovulation of a dominant follicle and the cow is then breed within one day of the administration of the second dose of hormone.

40 Claims, 1 Drawing Sheet

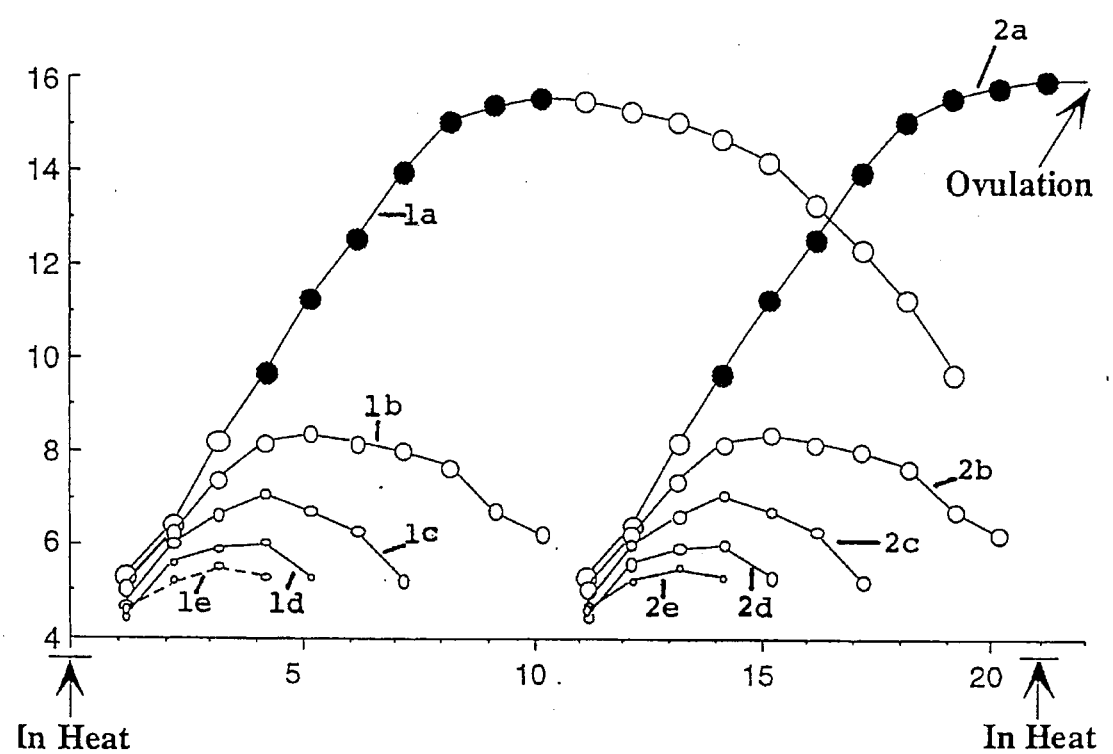

PROCESS FOR THE SYNCHRONIZATION OF OVULATION

FIELD OF THE INVENTION

This invention relates to the reproductive management of cows and more particularly processes for synchronizing ovulation in such cattle.

BACKGROUND OF THE INVENTION

The administration of hormones to control the reproductive process in domestic mammals such as horses, sheep, pigs, cows (bovine) and goats is well known in the art. One approach to managing reproductive processes in domestic mammals involves the direct administration of gonadotropins to domestic animals. Gonadotropins are produced by the anterior lobe of the pituitary gland and are characterized as follicle stimulating hormone (FSH) and luteinizing hormone (LH). Typically such hormones are extracted from porcine pituitary glands and employed in cattle or other domestic animals to control or enhance the ovulatory process. One gonadotropin preparation is the follicle stimulating hormone FSH-P available from Schering-Plough Corp. FSH-P has a relatively high and variable content of luteinizing hormone, and while effective in producing an ovulatory response, is less than desirable in terms of fertilization rates and production of transferable embryos. Another formulation which is effective in producing superovulation in cattle comprises a follicle stimulating hormone composition which contains a low, controlled amount of luteinizing hormone to produce a high ratio of follicle stimulating hormone to luteinizing hormone. This composition is disclosed in U.S. Pat. No. B1 4,780,451 to Donaldson.

As disclosed in the patent to Donaldson, the gonadotropin hormones FSH and LH can be administered to the animal by intramuscular or subcutaneous injection in order to stimulate follicular development in the ovaries. Gonadotropin treatment is usually started between days 9 and 13 of the estrous cycle. Two or three days after administration of the gonadotropin hormones, prostaglandin $F_{2\alpha}$ (or an analog), hereinafter referred to as $PGF_{2\alpha}$ is injected in order to terminate the luteal phase of the estrous cycle prematurely by lysing the corpus luteum. Estrous occurs about two days after regression of the corpus luteum and lasts about half a day followed by ovulation with fertilization of the ovum occurring a few hours after ovulation.

Gonadotropin releasing hormone (GnRH) can also be administered in order to stimulate ovulation. For example, U.S. Pat. No. 5,180,711 to Hodgen discloses the administration of gonadotropin releasing hormone (GnRH) subsequent to the administration of a GnRH antagonist administered in an amount effective to initially suppress gonadotropin levels. The GnRH antagonist, specifically antide, and the GnRH can be controlled to achieve a desired suppression of endogenous gonadotropins levels over an extended time interval.

SUMMARY OF THE INVENTION

In accordance with the present invention there is provided a method for synchronizing ovulation in cattle in order to provide for effective reproductive management and reduce excess open time for cattle herds. In carrying out the invention, a hormone selected from the group consisting of gonadotropin releasing hormone (GnRH), luteinizing hormone (LH), or human chorionic gonadotropin (hCG) is administered to an open cow during an estrous cycle in order to stimulate follicle development. After a suitable period of time to permit development of a dominant follicle, prostaglandin $F_{2\alpha}$ ($PGF_{2\alpha}$) is administered to initiate corpus luteum regression. Preferably the $PGF_{2\alpha}$ is administered about five to eight days, more specifically about seven days, after administration of the GnRH, LH or hCG to allow an appropriate maturation time for a dominant follicle induced by the GnRH injection. A second dose of GnRH, LH or hCG is then administered concomitantly with the $PGF_{2\alpha}$ injection or up to about three days after the $PGF_{2\alpha}$ injection. Preferably the second GnRH injection is scheduled to occur about one and one-half to two days after regression of the corpus luteum. This second dose of hormone functions to stimulate the ovulation of a dominant follicle and the cow is then bred about within one day subsequent to the administration of the second dose of hormone. Preferably breeding will occur about 16 to 20 hours after the second dose of GnRH, LH or hCG.

Preferably the GnRH is administered in the initial step and also the subsequent GnRH injection step in dose amount of less than 100 micrograms. In a more specific embodiment of the invention, the second dose of GnRH is administered in an amount which is less than the primary dose of GnRH. Usually relatively small quantifies of GnRH can be employed in both injection formats. More specifically, at least one of the doses of GnRH is administered in an amount within the range of 10–40 micrograms. The $PGF_{2\alpha}$ is administered in an amount within 20–30 milligrams per dose. The dose amounts as designated herein are for the hormones in their "native form" or in the case of analogs are designated as the equivalent amount of the hormone in question in the "native form."

In a further aspect of the invention, there is provided a method for synchronizing ovulation of cattle in large herds. Here, cows are selected from a herd by excluded pregnant cows or cows early in a lactating period to provide a selected group comprising a plurality of open cows. A first dose of GnRH, LH or hCG is administered to the selected group of cows and after a period time sufficient for the development of dominant follicles in the group cows, a dose of $PGF_{2\alpha}$ is submitted to the cows in the group. Thereafter, second doses of GnRH, LH or hCG are administered to the selected group of cows to stimulate ovulation of the dominant follicles. The cows are bred as a group, normally by artificial insemination with one day of administration of the second dose of GnRH, LH or hCG. The cows can be placed in groups near the end of their lactation periods, specifically, cows that are eight weeks postpartum in order to initiate the protocol. A week later, a second group of cows, again in the eighth postpartum week, can be selected until all of the cows in the group are under a synchronized ovulation regiment.

BRIEF DESCRIPTION OF THE DRAWING

The drawing is a graphical presentation of two waves of follicle growth as occurring during a bovine estrous cycle.

DETAILED DESCRIPTION OF THE INVENTION

Effective reproductive management of dairy cattle has become an important factor to dairy producers. The present invention provides a technique for managing reproduction in lactating dairy cattle by controlling the reproductive process with the sequential introduction of hormone. The invention allows for scheduled insemination of lactating dairy cattle. As explained below, by following the protocol of the present invention, artificial insemination (AI) in a herd can be regularly scheduled at one set time each week without the need for heat detection and with an attendant in days open.

As will be understood by those skilled in the art, the significant factors in the reproductive process in cattle can be summarized as follows. For pregnancy to occur, live sperm must be present in the reproductive tract at the time of ovulation or egg release. Ovulation occurs about one day after the first signs of heat. In natural service, the bull introduces the sperm during the time the animal is showing heat. Successful use of artificial insemination requires that semen be placed in the reproductive tract close to the time of ovulation. Thus, producers watch for signs of heat because this is the best indication that the animal is close to ovulation. However, only about 50% of heats are detected on an average dairy farm. Recognizing that improvement in heat detection can significantly increase reproductive efficiency of artificial insemination, several research approaches have attempted to improve heat detection programs.

As is well known in the art, normal regression of the corpus luteum at anestrous is due to secretion of the hormone prostaglandin $F_{2a}$ ($PGF_{2a}$) from the non-pregnant uterus. This hormone is commercially available (from UpJohn Co. under the mark Lutalyse and from Pitman-Moore under the mark Estrumate) and it is a common practice to use $PGF_{2a}$ to reduce the intervals between heats and improve heat detection efficiency. However, $PGF_{2a}$ does not regress the early corpus luteum, normally characterized at less than 7 days after heat. Thus it has been the practice to employ two injections of $PGF_{2a}$, fourteen days apart, in order to effectively synchronize heats in lactating cows. However, even after two injections of $PGF_{2a}$, lactating cows may show heat over a 7 day period. Thus, prescheduled inseminations are not very effective in lactating cows after $PGF_{2a}$ injections and producers must still carefully watch for signs of heat to determine the proper time of breeding.

Recent research results concerning follicle growth can be used to explain the reasons for the variability in the time from the second injection of $PGF_{2a}$ to heat. This can be explained in forms of "follicular waves." Over the past 10 years, ultrasound has been used to evaluate the changes on the ovary during the normal reproductive cycle. It was found that a group of 4–15 follicles, called a "follicular wave," began growing on the ovary about every 10 days. In a follicular wave, one follicle will grow faster than other follicles and will become what is known as the dominant follicle. The dominant follicle that is present at the time of corpus luteum regression will proceed to ovulation.

The drawing illustrates the growth of follicles during a 21 day estrous cycle for a cow in which two follicular waves developed during the estrous cycle. In FIG. 1, it is assumed that 5 follicles developed in each follicular wave. The follicle diameter, F,D, in millimeters is of the first group of follicles plotted on the ordinate as curves 1a, 1b, 1c, 1d and 1e against time, T, in days on the abscissa. The diameter of the second group of follicles, the second follicular wave, is plotted as curves 2a, 2b, 2c, 2d and 2e. As shown in the drawing, during the first follicular wave, the follicle depicted by curve 1a became a functionally dominant follicle at about the fourth day of the cycle as indicated by the shaded data points. The dominant follicle of the first follicular wave fails to ovulate because of progesterone from the corpus luteum. At the eleventh day after the previous estrous period, the second follicular wave is initiated and about three days later a second dominant follicle develops as indicated by the shaded data points in curve 2a. The animal goes in heat at day 21 and ovulation occurs. While a 21 day estrous cycle is shown it will be recognized by those skilled in the art that shorter or longer estrous cycles may be involved. Also, while two follicular waves are common, cows can have three follicular waves during an estrous cycle. Typically the estrous cycle of a bovine cow will range in length from about 18 to 24 days. The cow typically may be in heat for a period of 1 to 2 days.

Still referring to the drawing, if $PGF_{2a}$ is given at a time when a large dominant follicle is present then the animal will show heat in 2–3 days. This is because it does not take long for the follicle to grow to a size that secretes enough estrogen to cause the cow to show signs of heat. On the other hand, if $PGF_{2a}$ is given at a time when a new follicular wave is just beginning, then 6–7 days are required for the follicle to grow large enough to induce signs of heat in the cow. In view of the foregoing, it is to be recognized that a synchronization protocol that would allow for effective timed insemination of cows must not only control the corpus luteum but must also synchronize follicular waves.

The present invention employs the synchronized administration of hormones to control the two major structures of the ovary, the follicle and the corpus luteum. The first hormone administered is selected from the group consisting of gonadotropin releasing hormone (GnRH), luteinizing hormone (LH) and human chorionic gonadotropin (hCG). The second hormone employed in the present invention is $PGF_{2\alpha}$. The invention will be described initially with reference to the use of GnRH which is administered in two doses, a first dose to initiate a follicular wave and a second dose to ovulate a dominant follicle. However, as will be described in detail later, either hCG or LH can be employed in lieu of the GnRH. These hormones which exhibit luteinizing activity and are sometimes referred to as "luteinizing hormone-like" activators can be employed as substitutes for the first dose of GnRH or the second dose of GnRH or for both doses. Thus, the first dose may be luteinizing hormone and the second dose human chorionic gonadotropin or visa versa. One dose may be GnRH and the other dose LH or hCG or the LH or hCG may be used in both the first and second doses. As noted above, the invention will be described initially with respect to GnRH. This hormone is available commercially from Abbott Laboratories as Cysterlon or from American Home Products as Facterel.

In using this hormone, the preferred protocol is as follows. An initial injection of GnRH is given to the cows at any stage of the estrous cycle. The GnRH is administered in an amount sufficient to stimulate ovarian follicle development. After a period of time sufficient for development of a dominant follicle, normally about 5–8 days, $PGF_{2\alpha}$ is injected to regress the corpus luteum. A satisfactory and preferred standard interval for injection of the $PGF_{2\alpha}$ is seven days after initial injection of the GnRH. Concomitantly with the $PGF_{2\alpha}$ injection or within a period of up to three days thereafter, the second injection of GnRH is given to ovulate the follicle. The animals are then bred. Breeding can occur concomitantly with the GnRH injection, actually several hours before or after the GnRH injection, up to about one day after the second injection of GnRH. A suitable injection period can occur 16–20 hours after injection of the GnRH. However, as explained below, advantages can result from breeding fight at the time of the second dose of GnRH or even within a period of up to eight hours prior to or subsequent to injection of the second dose of GnRH.

A suitable protocol, together with a brief description of the purpose of the hormone injections is shown below by the following diagram:

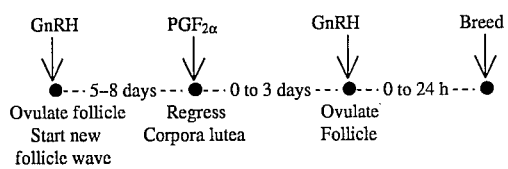

As described in greater detail below, the GnRH can be substituted with a GnRH analog or LH or hCG or analogs thereof. The $PGF_{2\alpha}$ can likewise be substituted analog with analogs of $PGF_{2\alpha}$.

While the normal practice will be to inseminate the cows about 16–20 hours after the second GnRH injection, insemination can occur any time ranging from the time of the GnRH injection or a day before or up to about a day later. Ovulation need not occur before insemination since the sperm can survive in the reproductive track for up to one or even two days after insemination. Thus insemination can safely take place one day before the GnRH injection. Preliminary work has shown that in some cases there may be some advantages to carrying out the artificial insemination concomitantly with the administration of the second dose of GnRH or within eight hours either before or after the second dose of GnRH. Where insemination occurs near or at the same time as GnRH injection, there appears to be a enhancement in the birth rate of female calves and, in addition, a somewhat lower spontaneous abortion rate.

The sequential hormone treatments function in the following manner. The first injection of GnRH (or the LH or hCG if used) will cause ovulation of any large functional follicles that are present on the ovaries. Experimental work has shown that a follicle will ovulate in over 80% of lactating dairy cows that are given this GnRH injection. This ensures that a Corpus Luteum is present on the ovary to inhibit animals from coming into heat during the following week. This injection causes growth of a new wave of follicles due to secretion of follicle stimulating hormone (FSH) from the pituitary gland. Thus, the first injection of GnRH assures the presence of a corpus luteum and synchronizes the growth of a new follicular wave. The follicle that will eventually ovulate will come from this new wave of follicles.

As with other protocols, such as disclosed in the aforementioned patent to Donaldson, the injection of $PGF_{2a}$ is designed to regress any corpora lutea that are present on the ovary. This allows the new dominant follicle to proceed toward ovulation. Usually about 1½ to 2 days later, just before two animals would begin to show signs of heat, the cows are given a second injection of GnRH. At this time the new dominant follicle should be at a large ovulatory size and this injection will cause the large follicle to ovulate. However, as indicated previously, the second dose of GnRH can be given at the same time as the $PGF_{2a}$ injection and this can be done where it is desirable to enhance management efficiency; that is by combining the $PGF_{2a}$ and GnRH injection, one step in the treatment protocol is eliminated. The cows will ovulate at 1–2 days, usually 24–32 hours after this second injection of GnRH. Thus, instead of having animals show heat over a 7 day period of time, ovulation can be synchronized to an 8 hour period of time. This concise synchronization allows for effective timed insemination.

At the start of a normal heat, the brain secretes large amounts of GnRH that in turn causes a release of luteinizing hormone (LH) which will cause ovulation of the Graafian follicle in about 24–32 hours. By following the present invention, the GnRH injection is given before the normal GnRH secretion and causes the follicle to proceed toward ovulation. Experimental work has shown that, only about 30% of cows will show behavioral signs of heat after using this protocol. Thus, this invention can be said to synchronize ovulation rather than synchronizing estrus. Experimental work as outlined below illustrates the synchronization protocol of the present invention for lactating dairy cows.

There are various approaches to using synchronization of ovulation for reproductive management of lactating dairy cows. The present invention can be applied in a manner to completely eliminate heat detection on a farm. In this scheme, all animals that are open can begin to receive the synchronization protocol. To simplify record-keeping, all animals in a herd can begin the protocol on a designated day of the week, e.g. Monday. By way of example, on an experimental dairy farm where research respecting the invention has been carried out, all cows that are greater than 57 days postpartum are started on the protocol. The preferred protocol requires 9–10 days from inception to breeding and by applying a 10 day period, all animals are bred between 67–73 days postpartum. There is no need to set an excessively early time for first insemination with this schedule because all animals will be synchronized and inseminated on the designated day. In other words, instead of choosing a voluntary waiting period as practiced in the prior art, the producer can designate a day of first insemination. For example, if the hormone injection regimen is started on a Monday, artificial insemination can be carried out on Thursday of the following week.

Experimental work carried out for the present invention involves a comparison of the use of the above described 10-day protocol without any estrous detection to standard reproductive management. This study involved 333 cows on three commercial dairy farms. The animals that were on the synchronization protocol had the same conception rate as the control animals (about 40%) and had 23 fewer days open (98 days vs. 121 days). As will be recognized by those skilled in the art, these farms had good reproductive management programs since the 121 days open for the control group is less than the open days average for a dairy farm, about 135 days. Thus, even on well-managed dairy farms the present invention can substantially reduce days open without any heat detection.

The present invention requires an initial determination as to when an animal is not pregnant and should be re-synchronized for a subsequent artificial insemination. If heat detection is not used, then this determination must be made on the basis of pregnancy diagnosis. In experimental work respecting the invention, an ultrasound machine has been used to determine pregnancy at an early stage, i.e. 24–32 days after conception. Since some veterinarians are currently using ultrasound this could be used to implement the invention.

This synchronization procedure of the present invention can be combined with heat detection. For example, the synchronization protocol can be used once-a-week on all eligible open cows and any cows that show heat can be bred by the "AM-PM" method. Another example of how producers can use heat detection and AM-PM breeding together is to set up all cows on a three week schedule. Every three weeks all open animals, not bred, and greater than 60 days postpartum can be synchronized following the protocol of the present invention to assure their breeding in 10 days. Any animals detected in heat around 21 days after the initial synchronization date would be assumed not pregnant and be re-bred. At about 32 days after the initial synchronization, the animals would have pregnancy diagnosis performed, preferably ultrasound scanning, and non-pregnant animals would be re-synchronized and bred for a second time at 42 days after the first breeding. Thus all animals will be bred every 42 days and animals that are detected in heat will be re-bred at shorter intervals.

While effective for previously bred cows, the synchronization protocol of the present invention does not appear to reduce open days for heifers nor does this protocol improve conception rates as such. A study to evaluate conception rates in cows and heifers was conducted as a collaborative effort between the experiment stations of Iowa, Kansas, Ohio, Missouri and Wisconsin sponsored by the USDA Cooperative States Research Service (Project NC-113, Methods to Improve Reproduction in Cows Postpartum). In this study, it was found that conception rates averaged about 40% for lactating dairy cows regardless of whether animals were bred to a standing estrus or after synchronization of ovulation. On the other hand, dairy heifers averaged about a 75% conception rate if bred to a standing heat, but a conception rate of only 35% after synchronization of ovulation. Thus, conception rates in heifers were much better than cows when breeding after a standing heat. However, the synchronization of ovulation protocol did not appear to result in efficient timed-insemination of heifers. While normal conception rates can be expected after applying the invention in lactating dairy cows, the invention should reduce days open by about one estrous cycle. A greater reduction might be expected if days open on a dairy farm are greater than 120 days. Particular attention should be paid to identifying the cows that do not conceive after each breeding. These animals may be re-synchronized and re-bred.

In the experimental work reported above, the first and second applications of GnRH were each administered in an amount of 100 microgram doses. This is consistent with the prior art usage of GnRH to stimulate ovulation. As explained below, the dose level from the first dose to the second dose can be, and normally will be, reduced. As a practical matter, it is believed that the dose rate can be reduced substantially to perhaps one-fourth of the standard 100 microgram doses. Based upon the experimental work concerning hormone doses that has been conducted thus far, it is believed that the preferred amount of both the first and second GnRH doses should be within the range of 10–50 micrograms with, as noted previously, the second dose being somewhat lower than the first dose. The differentiation of the first and second dose levels results from the fact that when the first dose of the GnRH is applied to initiate the synchronization protocol, the progesteron level in the cow will be relatively high. As a result, the response of the pituitary gland in releasing follicle stimulating hormone and luteinizing hormone would be somewhat reduced. When the second dose of GnRH is administered some 8–9 days later, the cows progesteron level will be relatively low and the estrogen level relatively high. Accordingly, a lower dose of GnRH can be applied at the second administration of this hormone.

The $PGF_{2\alpha}$ will normally be applied at a dose level of 25 milligrams which is consistent with the normal use of this hormone to terminate the luteal phase of the estrous cycle. While this may vary somewhat, normal practice should be to keep the $PGF_{2\alpha}$ dose within the range of about 20–35 milligrams.

The dosages described above are with respect to the hormones as they occur in the native form since these forms have FDA approval for use in meat and dairy animals. Analogs may be used, subject to the requirements for FDA approval, and, as will be recognized by those skilled in the art, such analogs may be used in smaller amounts to correspond to their higher activities.

By the term "native form" is meant the hormone having the same amino acid sequence and the same activity scale as found in nature. Thus, the native form of GnRH will include the form of the hormone, regardless of how synthesized, which as it produced by the hypothalamus. Thus the previously identified GnRH available under the marks Cystorelin or Factrel, are synthetic products of the same amino acid sequences and activities as naturally occurring in the animal, are considered to be the native form of the hormone. The dosage rates given herein are for the native form and corresponding adjustments should be made for analogs of different amino acid sequences having higher activities. Thus, the aforementioned range of 10–40 micrograms of GnRH is the dose rate for the native form of the hormone and for an analog having 10 times the activity of the native form, this range would designate a dose rate for such an analog of 1–4 micrograms.

Where luteinizing hormone or human chorionic gonadotropin are employed in lieu of GnRH to cause follicle ovulation, these hormones may be used in the amounts in which they have been used in the art to stimulate rupture and ovulation of a graafian follicle. However, as is the case with the GnRH, these hormones may be used in somewhat lower amounts than they are used in conventional practice. For example, hCG is normally used in amounts of about 5,000 to 10,000 international units (IU). In this application of the invention, it can of course be used in these amounts, but can also be used in lower amounts ranging down to perhaps 1,000 international units (IU). The luteinizing hormone dosage can be conveniently defined in terms of National Institute of Health S1 units as described, for example, in the aforementioned patent to Donaldson. Normally, the luteinizing hormone will be employed in about 5–15 NIH-LH-S1 units. As in the case of the GnRH, analogs of the LH and hCG can be used and adjustments made to accommodate different activities of the analogs as compared to the native hormones.

Having described specific embodiments of the present invention, it will be understood that modifications thereof may be suggested to those skilled in the art, and it is intended to cover all such modifications as fall within the scope of the appended claims.

What is claimed:

1. A method for synchronizing ovulation in cattle, the steps comprising:

(a) administering a first dose of a hormone selected from the group consisting of a gonadotropin releasing hormone (GnRH), a luteinizing hormone (LH) and a human chorionic gonadotropin (hCG), to an open cow during an estrous cycle in an amount effective to stimulate ovarian follicle development;

(b) subsequent to step (a) and after a period of time sufficient for development of a dominant follicle, administering a dose of prostaglandin $F_{2\alpha}$ ($PGF_{2\alpha}$) in an amount effective to initiate corpus luteum regression;

(c) concomitantly with or within a period of 3 days subsequent to step (b), administering a second dose of a hormone selected from the group consisting of LH, hCG and GnRH to stimulate ovulation of said follicle; and (d) concomitantly with or within one day prior to or subsequent to step (c), breeding said cow.

2. The method of claim 1, wherein said cow is a lactating cow.

3. The method of claim 2, wherein said dose of $PGF_{2\alpha}$ is administered about five to eight days after the first dose of hormone in step (a).

4. The method of claim 3, wherein said dose of $PGF_{2\alpha}$ is administered about seven days after the first dose of hormone in step (a).

5. The method of claim 3, wherein said second dose of hormone in step (c) is administered about 1½ to 2 days after administration of said dose of $PGF_{2\alpha}$.

6. The method of claim 3, wherein said cow is bred within a period extending from eight hours before to eight hours after the administration of said second dose of hormone in step (c).

7. The method of claim 3, wherein said cow is bred about the same time as the administration of said second dose of hormone in step (c).

8. The method of claim 4, wherein said cow is bred within a period of about 16–20 hours after the administration of said second dose of hormone in step (c).

9. The method of claim 1, wherein the hormone administered in step (a) is GnRH.

10. The method of claim 9, wherein the hormone dose administered in step (c) is GnRH.

11. The method of claim 9, wherein the GnRH in step (a) is administered in an amount of less than 100 micrograms.

12. The method of claim 11, wherein the second dose of GnRH administered in step (c) is administered in an amount of less than 100 micrograms.

13. The method of claim 12, wherein said $PGF_{2\alpha}$ dose is about 20–35 milligrams.

14. The method of claim 10, wherein said second dose of GnRH is administered in step (c) in an amount which is less than the first dose of the GnRH administered in step (a).

15. The method of claim 10, wherein at least one of the doses of GnRH is administered in an amount within the range of 10–40 micrograms.

16. The method of claim 15, wherein said second dose of GnRH in step (c) is administered in an amount which is less than the first dose of the GnRH administered in step (a).

17. The method of claim 1, wherein at least one of said doses of hormone administered in steps (a) and (c) is selected from the group consisting of LH and hCG.

18. The method of claim 17, wherein the other of said doses of hormone administered in steps (a) and (c) is selected from the group consisting of LH and hCG.

19. The method of claim 1, wherein said first and second doses of hormone administered in steps (a) and (c) are luteinizing hormone.

20. The method of claim 1, wherein said first and second doses of hormone administered in steps (a) and (c) are human chorionic gonadotropin.

21. A method for synchronizing ovulation of cattle, the steps comprising:

(a) selecting a group of cows comprising a plurality of open cows;

(b) administering a first dose of a hormone selected from the group consisting of a gonadotropin releasing hormone (GnRH), a luteinizing hormone (LH) and a human chorionic gonadotropin (hCG), to said cows during estrous cycles in an amount effective to stimulate ovarian follicle development;

(c) subsequent to step (b) and after a period of time sufficient for development of dominant follicles in said group of cows, administering prostaglandin $F_{2\alpha}$ ($PGF_{2\alpha}$) to said selected group of cows to initiate corpus luteum regression;

(d) concomitantly with or within a period of 3 days subsequent to step (c), administering a second dose of hormone selected from the group consisting of GnRH, LH and (hCG) to stimulate ovulation of said dominate follicles; and (e) concomitantly with step (d) or within one day of the administration of said dose of GnRH in step (d), breeding said group of cows.

22. The method of claim 21, wherein said cows are lactating cows.

23. The method of claim 22, wherein the hormone in step (b) is GnRH administered in an amount of less than 100 micrograms per dose.

24. The method of claim 23, wherein said hormone in step (d) is GnRH and the second doses of GnRH in step (d) are administered in amounts of less than 100 micrograms per dose.

25. The method of claim 24, wherein said second doses of GnRH in step (d) are administered in amounts which are less than the first doses of the GnRH administered in step (b).

26. The method of claim 24, wherein at least one of the doses of the GnRH is administered in an amount within the range of 10–40 milligrams.

27. The method of claim 21, wherein individual cows within said selected group are at different stages in their estrous cycles.

28. The method of claim 27, wherein said cows are lactating cows.

29. The method of claim 21, wherein said doses of $PGF_{2\alpha}$ are administered about five to eight days after the first dose of hormone in step (a).

30. The method of claim 21, wherein said second dose of hormone in step (d) is administered about 1½ to 2 days after administration of said dose of $PGF_{2\alpha}$.

31. The method of claim 21, wherein said cow is bred within a period extending from eight hours before to eight hours after the administration of said second dose of hormone in step (d).

32. The method of claim 21, wherein said cow is bred about the same time as the administration of said second dose of hormone in step (d).

33. The method of claim 21, wherein said cows are bred within a period of about one day after the administration of said second dose of hormone in step (d).

34. The method of claim 21, wherein the hormone administered in step (b) is GnRH.

35. The method of claim 34, wherein the hormone dose administered in step (d) is GnRH.

36. The method of claim 21, wherein said second doses of GnRH are administered in step (d) in amounts which are less than the first doses of the GnRH administered in step (b).

37. The method of claim 21, wherein at least one of said doses of hormone administered in steps (a) and (d) is selected from the group consisting of LH and hCG.

38. The method of claim 37, wherein the other of said doses of hormone administered in steps (a) and (d) is selected from the group consisting of LH and hCG.

39. The method of claim 21, wherein said first and second doses of hormone administered in steps (a) and (d) are luteinizing hormone.

40. The method of claim 21, wherein said first and second doses of hormone administered in steps (a) and (d) are human chorionic gonadotropin.

* * * * *